(12) United States Patent
Dalseno

(10) Patent No.: US 11,701,381 B2
(45) Date of Patent: Jul. 18, 2023

(54) COMPOSITION FOR THE TREATMENT OF THE ORAL CAVITY

(71) Applicant: FADIM LTD, Mellieha (MT)

(72) Inventor: Andrea Dalseno, Mellieha (MT)

(73) Assignee: FADIM Ltd, Naxxar (MT)

( * ) Notice: Subject to any disclaimer, the term of this patent is extended or adjusted under 35 U.S.C. 154(b) by 92 days.

(21) Appl. No.: 17/276,503

(22) PCT Filed: Sep. 13, 2019

(86) PCT No.: PCT/EP2019/074478
§ 371 (c)(1),
(2) Date: Mar. 16, 2021

(87) PCT Pub. No.: WO2020/058113
PCT Pub. Date: Mar. 26, 2020

(65) Prior Publication Data
US 2022/0031733 A1  Feb. 3, 2022

(30) Foreign Application Priority Data

Sep. 18, 2018 (IT) .................. 102018000008670

(51) Int. Cl.
*A61K 31/728* (2006.01)
*A61K 9/00* (2006.01)
*A61K 36/61* (2006.01)
*A61K 47/22* (2006.01)

(52) U.S. Cl.
CPC ............ *A61K 31/728* (2013.01); *A61K 9/006* (2013.01); *A61K 36/61* (2013.01); *A61K 47/22* (2013.01)

(58) Field of Classification Search
CPC ...... A61K 31/728; A61K 9/006; A61K 36/61; A61K 47/22
USPC ......................................................... 514/54
See application file for complete search history.

(56) References Cited

FOREIGN PATENT DOCUMENTS

| CN | 103417581 A | | 12/2013 |
|---|---|---|---|
| CN | 107998107 A | | 5/2018 |
| GB | 2453157 A | * | 4/2009 |
| WO | 2014202851 A1 | | 12/2014 |

OTHER PUBLICATIONS

Syed et al. Allergic Reactions to Dental Materials—A Systematic Review. Journal of Clinical and Diagnostic Research. Oct. 2015, vol. 9(10): ZE04-ZE09. (Year: 2015).*
Supplement Police, Unique Manuka Factor—Best 70% Pure UMF Products& Supplements? Feb. 21, 2017. https://supplementpolice.com/unique-manuka-factor/ (Year: 2017).*
Neuman et al. Hyaluronic Acid and Wound Healing. J Pharm Pharm Sci (www.cspsCanada.org) 18(1) 53-60, 2015. (Year: 2015).*
Tenci Marika et al.: "Application of DoE approach in the development of mini-capsules, based on biopolymers and makuka honey polar fraction, as powder formulation for the treatment of skin ulcers"; International Journal of Pharmaceutics, vol. 516, No. 1; Oct. 24, 2016.
Database WPI; Week 201420; Thomson Scientific, London, Great Britain; AN 2014-014427; 2014.
Database WPI; Week 201849; Thomson Scientific, London, Great Britain; AN 2018-365662; 2018.
Chen Chien-Chia et al; "Investigations of kanuka and manuka essential oils forin vitrotreatment of disease and cellular inflammation caused by infectious microorganisms"; Journal of Microbiology, Immunology and Infection, vol. 49, No. 1, Feb. 28, 2014.
Yoo Yeong Wol et al.; "Chemical Composition and in vitro Antimicrobial and Antioxident Activities of Commercially Available Essential Oils against Multidrug Resistant Bacteria"; Journal of Life Science, Korean Intellectual Property Office; Mar. 30, 2014.

* cited by examiner

*Primary Examiner* — Yih-Horng Shiao
(74) *Attorney, Agent, or Firm* — Dickinson Wright PLLC; Andrew D. Dorisio

(57) ABSTRACT

A composition for the prevention and treatment of the oral cavity comprising hyaluronic acid and a Manuka-derived product is described. The composition of the invention stabilizes the hyaluronic acid protecting the same from the aggression of the hyaluronidase present in the oral cavity, in particular on the mucous membranes and on the gingival walls, thus increasing the overall efficacy and the therapeutic effect.

15 Claims, No Drawings

COMPOSITION FOR THE TREATMENT OF THE ORAL CAVITY

FIELD OF THE INVENTION

The present invention relates to a composition for the prevention and treatment of the oral cavity comprising hyaluronic acid and a Manuka-derived product.

STATE OF THE ART

The multiple biochemical and pharmacological properties of hyaluronic acid have long been known. These properties make hyaluronic acid a product of great efficacy and enormous potential for dentistry; its healing and regenerating connective tissue properties are widely used for the treatment of surgical or traumatic wounds. The anti-inflammatory and anti-oedema effects together with the ability to form a protective barrier, support and characterize its efficacy in the treatment of periodontopathies and in diseases of the oral mucosa such as aphthous stomatitis.

But what emerges from the analysis of the most recent literature is that, unlike other sectors, dental use requires particular attention for the presence in the oral cavity of opportunistic microorganisms, some of which are highly virulent, that can significantly modify the response to treatment with hyaluronic acid.

The use of hyaluronic acid in dentistry requires some preliminary observations as the oral cavity constitutes an ecosystem formed by very different habitats. It is also characterized by high dynamism due to the continuous elimination and introduction of bacteria and food. The microbial ecology of the oral cavity is, together with that of the intestinal tract, one of the richest and most complex of our organism and the mouth is populated by opportunistic microorganisms perfectly adapted to the environment. Over 300 species are able to colonize the mouth and in individuals it is possible to demonstrate on average 150-200 species. This indicates that any modification, either physiological or pathological, of the oral mucosa must interact with the resident bacterial flora.

Certainly, diet and personal physical conditions are factors that contribute to influencing the oral ecosystem, but locally the most important are: the presence of plaque, saliva and crevicular fluid, the results of odontostomatological interventions, oral hygiene.

In normal supragingival biofilm, the bacterial load is low, Gram-positive species predominate and Gram-negative species are rare. Under these normal conditions and in the absence of risk factors, the growth of a biofilm that does not contain recognized oral pathogens can be contrasted by the organism.

The acquisition of specific etiological agents of bacterial origin breaks this balance and there is an abnormal and pathological increase in biofilm with a very high bacterial load and consequent plaque formation. The most frequent periodontal diseases such as gingivitis and periodontitis, which develop with the increase in plaque accumulation, therefore acknowledge an infectious etiopathogenesis.

The microorganisms are thus able to produce very differentiated virulence chemical factors that stimulate the appearance of deep local inflammatory events accompanied by the induction of high specific antibody levels.

The adhesion between the bacteria, the coaggregation and the synergism that is created, is the main mechanism of virulence.

A special role is played by collagenases, metalloproteinases and hyaluronidases, as they are active on the extracellular matrix of connective tissue: collagenase, for example, is able to break up collagen fibres, hyaluronidases (hyaluronate lyases), as already mentioned, depolymerize the hyaluronic acid of the gingival epithelium thus reducing its viscosity and facilitating the diffusion of microorganisms in the tissues.

Hyaluronidases are present in almost all prokaryotic and eukaryotic species, while, unlike the enzyme produced by bacteria (hyaluronate lyase), human hyaluronidase is present in different isoforms in the body hypothesizing a specificity of localization and effects. Historically, it is called "spreading factor" because, by causing the hydrolysis of hyaluronic acid, it facilitates the spread of toxins.

The enzyme hyaluronidase has recently held a great interest for its involvement in many pathological conditions, including some infectious processes. For example, it was shown that the most virulent strains of *S. pneumoniae* showed the highest hyaluronidase production, so it was hypothesized that hyaluronidase inhibition could be an important factor in the control of pneumococcal invasion.

The hyaluronidases produced by the plaque bacteria can therefore represent a strong virulence factor that directly involves the gingival epithelium and its main structural component, namely hyaluronic acid.

The depolymerization of hyaluronic acid, induced by the hyaluronidases of the microbial flora present in the bacterial plaque, profoundly alters the structure of the gingival connective tissue, favouring bacterial infiltration and therefore triggering the infectious process underlying the periodontal diseases.

As said, the clinical evidence have confirmed the effectiveness of the application of hyaluronic acid in the healing and tissue regeneration processes, while for the treatment of periodontopathies, despite the many clinical evidence confirm a clear efficacy in the acute episodes, for the chronic evolution of the disease further confirmations are still required through more substantial clinical trials.

However, in the case of gingivitis or periodontitis, the microbial ecosystem of the oral cavity and the bacterial plaque continuously expose hyaluronic acid (both endogenous and exogenously administered) to bacterial aggression which, in conditions of gum tissue or oral mucosa suffering, progressively reduces the biological effects, so that in clinical practice the antibiotics are frequently used to reduce the pathogenicity of the bacterial flora. The availability of formulations almost exclusively for systemic administration unfortunately limits the actual local effectiveness. It is therefore evident the interest for curative and conservative interventions also on the same homeostasis of the gingival tissue for local application in order to protect hyaluronic acid from bacterial aggression directly in the oral cavity.

It would therefore be extremely desirable to apply exogenous hyaluronic acid together with active ingredients able to reduce the adhesiveness or penetration of bacteria so as to intervene in a clinically more effective way than the simple treatment with hyaluronic acid, at the same time avoiding the use of antibiotics, which, as well known, can trigger antibiotic-resistance phenomena over time.

It is therefore an object of the present invention to provide a solution to the problem of the depolymerization of hyaluronic acid induced by hyaluronidases of the microbial flora present in the bacterial plaque.

SUMMARY OF THE INVENTION

This object has been achieved by a composition comprising hyaluronic acid and a Manuka-derived product, as reported in claim 1.

In another aspect, the present invention relates to the use of this composition for the prevention and treatment of diseases of the oral cavity.

As will be clear from the following detailed description and the embodiments provided for illustrative and non-limiting purposes, the composition of the invention surprisingly allows to stabilize the hyaluronic acid protecting the same from the aggression of the hyaluronidase present in the oral cavity, in particular on the mucous membranes and on the gum walls.

The characteristics and the advantages of the present invention will become clear from the following detailed description and the working examples provided for illustrative and non-limiting purposes.

DETAILED DESCRIPTION OF THE INVENTION

The invention therefore relates to a composition comprising hyaluronic acid and a Manuka-derived product selected from Manuka honey, Manuka essential oil and mixtures thereof.

The term 'Manuka', in the traditional Maori language, represents the *Leptospermum scoparium* plant, a dense evergreen shrub covered for many months with numerous pink, white and dark red flowers, which are extremely attractive to bees and whose color depends on the quantity of chrome present in the soil.

The indigenous people of New Zealand, the Maoris, have for a long time passed on their knowledge about the healing properties of the Manuka shrub and only recently the government of New Zealand became aware of this treasure of knowledge and began to subsidize the Manuka oil trade.

Manuka honey is produced by bees that collect nectar from Manuka flowers, plants that have grown spontaneously for thousands of years in New Zealand. This full-bodied honey is appreciated for its high phenol content.

There is also honey deriving from the *Leptospermum polygalifolium* variety, of Australian origin, which has proved to be even more effective than the New Zealand one.

The antibacterial activity of Manuka honey is measured by two different indicators, namely MGO and UMF®.

MGO is an index that refers to the presence in Manuka honey of the methylglyoxal level (measured as mg/kg (ppm)), but which does not consider the non-peroxidic antibacterial activity. Methylglyoxal is a component present in the pollen of the flowers of the Manuka tree and is considered one of the distinctive elements of honey's antibacterial activity. UMF® (Unique Manuka Factor) is a registered international trademark that can only be used by authorized licensees that meet a number of well-defined criteria, including continuous review and monitoring to ensure that the product is natural and unadulterated. Only Manuka Honey that has non-peroxidic antibacterial activity can boast the UMF® trademark on the label.

The number UMF represents the three chemical markers that identify the content of Manuka honey and guarantee its origin, purity and quality:
Dihydroxyacetone DHA,
Methylglyoxal MGO,
Leptosperin (methyl syringate 4-O-β-D-gentiobiose).

To receive a UMF® classification, a honey must have the presence of all three chemical markers. The number UMF is a measure of the attributes and values that make up Manuka honey. A number UMF of 10+ is the minimum required to obtain the UMF® classification and therefore be considered effective. Honey that meets this minimum requirement is commonly referred to as "active Manuka honey". The number UMF has a 1:1 relationship with the phenol standard: a honey with a number UMF 10+ corresponds to a 10% phenol solution.

Manuka essential oil is extracted from leaves and twigs by steam distillation. Typically, a distillation time of 2 to 6 hours is required to extract 80-90% of oil from Manuka, due to the heavy components of the oil, or sesquiterpenes. Among the active ingredients present therein, the most important is linalool, a monoterpene. Manuka essential oil can be effectively used against bacteria, fungi and yeasts. It has anti-inflammatory, antiseptic, antifungal, antiviral, regenerating, antibiotic, germicidal and immunostimulant properties. The bactericidal activity of Manuka essential oil is up to 30 times higher than that of the known Tea Tree oil.

Preferably, Manuka honey for the purposes of the present invention has a number UMF of up to 20+. More preferably, Manuka honey has a number UMF of 10+ to 20+. It has surprisingly been found that the Manuka-derived product, in addition to its own several properties, allows to stabilize the hyaluronic acid by actively counteracting the aggression by the hyaluronidase, at the same time synergizing with it and therefore significantly increasing the therapeutic effect.

Preferably, the hyaluronic acid has a high molecular weight, i.e. 800-2000 kDa.

Preferably, said hyaluronic acid and said Manuka-derived product are in weight ratio of 5:1 to 1:300.

More preferably, said hyaluronic acid and said Manuka-derived product are in weight ratio of 1:3 to 1:100.

In preferred embodiments, said hyaluronic acid and said Manuka-derived product are in weight ratio of 1:1 to 1:25.

In some embodiments, the composition of the invention comprises up to 5 wt % of said hyaluronic acid, more preferably 0.1-5 wt %.

For the purposes of the present invention, unless otherwise specified, "wt %" means % by weight on the weight of the composition of the invention.

In preferred embodiments, the composition of the invention comprises 0.1-1 wt % of said hyaluronic acid.

In other embodiments, the composition of the invention comprises up to 15 wt % of said Manuka-derived product.

When said Manuka-derived product is Manuka honey or a mixture thereof with Manuka essential oil, the composition of the invention comprises 1-15 wt % of said Manuka honey, more preferably 3-10 wt %.

When said Manuka-derived product is Manuka essential oil or a mixture thereof with Manuka honey, the composition of the invention comprises 0.1-5 wt % of said essential Manuka oil, more preferably 0.1-1 wt %.

In other preferred embodiments, the composition of the invention comprises up to 5 wt % of said Manuka-derived product, more preferably 0.1-4.8 wt %. In such preferred embodiments, said Manuka-derived product is preferably Manuka honey having a number UMF of 10+ to 20+, or a mixture of Manuka essential oil and Manuka honey having a number UMF of 10+ to 20+.

The composition of the invention may further include at least one C10-C20 fatty acid ester of ascorbic acid. Such ascorbic acid derivatives have the advantage of benefiting from all the properties of vitamin C at the same time resulting more stable than the same, especially during the sterilization treatments of the final products containing hyaluronic acid.

Preferably, said at least one C10-C20 fatty acid ester of ascorbic acid is selected from ascorbyl laurate, ascorbyl myristate, ascorbyl palmitate, ascorbyl stearate and mixtures thereof.

In preferred embodiments, the composition of the invention further comprises ascorbyl palmitate.

Preferably, said hyaluronic acid and said at least one C10-C20 fatty acid ester of ascorbic acid are in weight ratio of 50:1 to 1:100.

More preferably, said hyaluronic acid and said at least one C10-C20 fatty acid ester of ascorbic acid are in weight ratio of 10:1 to 1:10.

In preferred embodiments, said hyaluronic acid and said at least one C10-C20 fatty acid ester of ascorbic acid are in weight ratio of 2:1 to 1:2.

In some embodiments, the composition of the invention comprises up to 5 wt % of said at least one C10-C20 fatty acid ester of ascorbic acid, more preferably 0.1-5 wt %.

In preferred embodiments, the composition of the invention comprises 0.1-1 wt % of said at least one C10-C20 fatty acid ester of ascorbic acid.

In preferred embodiments, the composition of the invention is in the form of a unit dose.

Preferably, this unit dose comprises up to 2 mg of said hyaluronic acid, more preferably 0.2-2 mg.

Preferably, this unit dose comprises up to 50 mg of said Manuka-derived product. In preferred embodiments, this unit dose comprises 5-50 mg of Manuka honey or 0.2-2 mg of Manuka essential oil, or both.

Preferably, this unit dose further comprises up to 2 mg of said at least one C10-C20 fatty acid ester of ascorbic acid, more preferably 0.2-2 mg.

It should be understood that the preferred aspects identified for the individual components are to be considered analogously preferred in the unit dose embodiments described above. The composition of the invention, even in the form of a unit dose, can further comprise pharmaceutically acceptable excipients. The term "excipient" means a compound or its mixture suitable for use in a formulation for the treatment of oral cavity diseases. For example, an excipient for use in a pharmaceutical formulation generally should not cause an adverse response in a subject, nor should it significantly inhibit the effectiveness of the composition.

Suitable excipients are acidifiers, acidity correctors, anti-agglomerants, antioxidants, bulking agents, resistance agents, gelling agents, coating agents, modified starches, sequestering agents, thickeners, sweeteners, diluents, disaggregants, glidants, dyes, binders, lubricants, stabilizers, adsorbents, humectants, aromas, film-forming substances, emulsifiers, wetting agents, release retardants and mixtures thereof.

Advantageously, the composition of the invention may be free of preservatives.

Preferably, said excipients are mineral oil, liquid paraffin, white vaseline, polyoxyethylene, emulsifying wax, stearyl alcohol, isostearyl alcohol, cetylstearyl alcohol, stearic acid, glyceryl stearate, sodium lauryl sarcosinate, glycerine, diethylene glycol monoethyl ether, polyethylene glycols, polyethylene glycols, Poloxamer 407, Macrogol 400, purified bentonite, myristyl propionate, dimethicone, titanium dioxide, anionic, cationic and non-ionic surfactants, water, potassium sorbate, sodium benzoate, ε-polylisine, sucralose, maltodextrin, citric acid, sodium carbonate, calcium carbonate, magnesium carbonate, magnesium stearate, natural starch, partially hydrolyzed starch, modified starch, lactose, calcium phosphate, calcium carbonate, calcium sulfate, polyvinylpyrrolidone, silica, colloidal silica, precipitated silica, magnesium silicates, aluminum silicates, sodium lauryl sulfate, magnesium lauryl sulfate, methacrylate copolymers, modified cellulose, calcium carboxymethyl cellulose, sodium carboxymethyl cellulose, microcrystalline cellulose, ethyl cellulose, gelatin, hydroxyethyl cellulose, hydroxypropyl cellulose, polydextrose, carrageenan, methyl cellulose, sucrose, sucrose esters, sorbitol, xylitol, dextrose, fructose, maltitol, gum tragacanth, pectin, agar-agar, carboxypolymethylene, hydroxypropyl methylcellulose, tragacanth, mannitol, or a mixture thereof.

In some embodiments, the composition of the invention consists essentially of hyaluronic acid and a Manuka-derived product selected from Manuka honey, Manuka essential oil and mixtures thereof, and optionally at least one C10-C20 fatty acid ester of ascorbic acid. The expression "consists essentially of" means that hyaluronic acid and Manuka-derived product, and optionally at least one C10-C20 fatty acid ester of ascorbic acid, are the only active ingredients in the treatment of oral cavity diseases to be present in the composition, while any additional components or excipients do not interfere with their action. It should be understood that all the aspects identified above as preferred and advantageous for the composition and its components are to be considered similarly preferred and advantageous also for these embodiments.

In other embodiments, the composition of the invention consists of hyaluronic acid, a Manuka-derived product selected from Manuka honey, Manuka essential oil and mixtures thereof, pharmaceutically acceptable excipients, and optionally at least one C10-C20 fatty acid ester of ascorbic acid.

The composition of the present invention can be prepared by methods known in the art. In fact, for topical administration, the components can, for example, be mixed as such or with one or more excipients, thus obtaining the composition of the invention preferably in the form of a solution, lotion, emulsion, suspension, gel, ointment, cream, paste, spray, solution, or combinations thereof.

More preferably, the composition of the invention is in the form of a gel.

In another aspect, the present invention relates to the use of the composition described above for the prevention and treatment of oral cavity diseases.

These diseases of the oral cavity include gingivitis, periodontitis, periodontitis, canker sores (also recurrent), mucositis, stomatitis, gum lesions, gum ulcers, dryness, halitosis, bleeding and gingival retraction.

The composition of the invention can be administered orally, buccally, or sublingually.

Preferably, the composition of the invention is for local topical use in the oral cavity.

More preferably, the composition of the invention is administered at least once a day. For the purposes of the present invention, the term "day" means a period of time of 24±2 hours.

In preferred embodiments, the composition of the invention is administered once or twice a day as a unit dose, as described above. More preferably, each administration provides for the application of a dose of 0.1-1 ml of composition, even more preferably 0.2-0.4 ml of composition.

It should be also understood that all the combinations of preferred aspects of the composition of the invention, as well as of the preparation processes, and uses of the same, as above reported, are to be deemed as hereby disclosed.

All combinations of the preferred aspects of the composition of the invention, preparation processes, and uses disclosed above are to be understood as herein described.

Below are working examples of the present invention provided for illustrative purposes.

EXAMPLES

Example 1

The following composition has been prepared:

| | |
|---|---|
| hyaluronic acid 1000 kDa | 0.2 wt % |
| Manuka honey UMF 20+ | 5 wt % |
| excipients | balance to 100% |

Example 2

The following composition has been prepared:

| | |
|---|---|
| hyaluronic acid 1000 kDa | 0.2 wt % |
| Manuka essential oil | 0.2 wt % |
| excipients | balance to 100% |

Example 3

The following composition has been prepared:

| | |
|---|---|
| hyaluronic acid 1000 kDa | 0.2 wt % |
| Manuka honey UMF 20+ | 5 wt % |
| ascorbyl palmitate | 0.2 wt % |
| excipients | balance to 100% |

Example 4

The following composition has been prepared:

| | |
|---|---|
| hyaluronic acid 1000 kDa | 0.2 wt % |
| Manuka essential oil | 0.2 wt % |
| ascorbyl palmitate | 0.2 wt % |
| excipients | balance to 100% |

Example 5

The following composition has been prepared:

| | |
|---|---|
| hyaluronic acid 1000 kDa | 0.2 wt % |
| Manuka honey UMF 20+ | 5 wt % |
| ascorbyl stearate | 0.4 wt % |
| excipients | balance to 100% |

Example 6

The following composition has been prepared:

| | |
|---|---|
| hyaluronic acid 1000 kDa | 0.2 wt % |
| Manuka essential oil | 0.2 wt % |
| ascorbyl stearate | 0.4 wt % |
| excipients | balance to 100% |

Example 7

The following composition has been prepared:

| | |
|---|---|
| hyaluronic acid 1000 kDa | 0.2 wt % |
| Manuka honey UMF 20+ | 5 wt % |
| Manuka essential oil | 0.2 wt % |
| ascorbyl palmitate | 0.4 wt % |
| excipients | balance to 100% |

The invention claimed is:

1. A method for treating an oral cavity disorder, the method comprising the topical administration to a subject in need thereof of a composition, consisting essentially of hyaluronic acid, at least one fatty acid C10-C20 ester of ascorbic acid, and 0.1-4.8 wt % of a Manuka-derived product selected from the group consisting of Manuka honey, Manuka essential oil, and mixtures thereof.

2. The method of claim 1, wherein said hyaluronic acid and said Manuka-derived product are in a weight ratio of 5:1 to 1:300.

3. The method of claim 1, wherein said composition has up to 5 wt % of said hyaluronic acid, based on the weight of the composition.

4. The method of claim 1, wherein said Manuka-derived product is Manuka honey.

5. The method of claim 1, wherein said Manuka-derived product is Manuka honey having a number UMF® of 10+ to 20+, or a mixture of Manuka essential oil and Manuka honey having a number UMF® of 10+ to 20+, where UMF means Unique Manuka Factor.

6. The method of claim 1, wherein said at least one fatty acid C10-C20 ester of ascorbic acid is selected from the group consisting of ascorbyl laurate, ascorbyl myristate, ascorbyl palmitate, ascorbyl stearate and mixtures thereof.

7. The method of claim 6, wherein said hyaluronic acid and said at least one fatty acid C10-C20 ester of ascorbic acid are in a weight ratio of 50:1 to 1:100.

8. The method of claim 6, wherein said composition has up to 5 wt % of said at least one fatty acid C10-C20 ester of ascorbic acid, based on the weight of the composition.

9. The method of claim 1, wherein said hyaluronic acid has a molecular weight of 800-2000 kDa.

10. The method of claim 1, wherein said composition is in the form of a unit dose having up to 50 mg of said Manuka-derived product.

11. The method of claim 10, wherein said unit dose has 5-50 mg of Manuka honey or 0.2-2 mg of Manuka essential oil, or both.

12. The method of claim 10, wherein said unit dose has up to 2 mg of said hyaluronic acid.

13. The method of claim 10, wherein said unit dose has up to 2 mg of said at least one C10-C20 fatty acid ester of ascorbic acid.

14. The method of claim 1, wherein said composition is in the form of a solution, lotion, emulsion, suspension, gel, ointment, cream, paste, or spray.

15. The method of claim 1, wherein said oral cavity disorder is selected from the group consisting of gingivitis periodontitis, pyorrhea, aphthae, recurrent aphthae, mucositis, stomatitis, gingival lesions, gingival ulcers, dryness, halitosis, bleeding, and gingival retraction.

\* \* \* \* \*